United States Patent
Negro et al.

(10) Patent No.: US 9,103,751 B2
(45) Date of Patent: Aug. 11, 2015

(54) DEVICE FOR TRANSVERSELY SUPPORTING A LONGITUDINAL TEST TUBE, AND EQUIPMENT FOR DETERMINING THE MECHANICAL BENDING PROPERTIES OF SUCH A TEST TUBE

(75) Inventors: Manuel Negro, Blagnac (FR); Victor Combes, Toulouse (FR); Laurent Huquet, Reze (FR); Marc Hell, Montastruc-la-Conseillere (FR)

(73) Assignee: Airbus Operations (SAS), Toulouse (FR)

( * ) Notice: Subject to any disclaimer, the term of this patent is extended or adjusted under 35 U.S.C. 154(b) by 53 days.

(21) Appl. No.: 14/119,511

(22) PCT Filed: Jun. 15, 2012

(86) PCT No.: PCT/EP2012/061467
§ 371 (c)(1),
(2), (4) Date: Feb. 17, 2014

(87) PCT Pub. No.: WO2012/175426
PCT Pub. Date: Dec. 27, 2012

(65) Prior Publication Data
US 2014/0150566 A1 Jun. 5, 2014

(30) Foreign Application Priority Data
Jun. 20, 2011 (FR) ..................................... 11 55389

(51) Int. Cl.
*G01N 3/20* (2006.01)
*G01N 3/04* (2006.01)

(52) U.S. Cl.
CPC .. *G01N 3/20* (2013.01); *G01N 3/04* (2013.01); *G01N 2203/0023* (2013.01); *G01N 2203/0264* (2013.01); *G01N 2203/0274* (2013.01)

(58) Field of Classification Search
CPC ... G01N 3/04; G01N 3/20; G01N 2203/0023; G01N 2203/0264; G01N 2203/0274
USPC ............................................ 73/849, 852, 856
See application file for complete search history.

(56) References Cited

U.S. PATENT DOCUMENTS

| 4,986,132 | A | | 1/1991 | Calomino | |
|---|---|---|---|---|---|
| 5,127,271 | A | * | 7/1992 | Sato et al. | 73/852 |
| 5,231,882 | A | | 8/1993 | Bertele et al. | |
| 5,699,274 | A | * | 12/1997 | Starostovic, Jr. | 73/849 |
| 6,053,052 | A | * | 4/2000 | Starostovic | 73/851 |
| 6,918,306 | B1 | * | 7/2005 | Cavallaro et al. | 73/849 |
| 2011/0167922 | A1 | * | 7/2011 | Krause et al. | 73/808 |

* cited by examiner

FOREIGN PATENT DOCUMENTS

FR 2937731 4/2010

OTHER PUBLICATIONS

French Search Report, Aug. 9, 2012.

*Primary Examiner* — Lisa Caputo
*Assistant Examiner* — Jonathan Dunlap
(74) *Attorney, Agent, or Firm* — Greer, Burns & Crain Ltd.

(57) ABSTRACT

A device for the transverse retention of a longitudinal test specimen and apparatus for the mechanical characterization in bending of such a test specimen. The test specimen includes a web and at least one main flange connected to one end of said web. The device includes a body in which there is formed a housing which is shaped to house said test specimen transversally and which has a main bearing face against which one face of said web is intended to press; and a mobile clamp formed so as to press said web against said main bearing face.

13 Claims, 3 Drawing Sheets

DEVICE FOR TRANSVERSELY SUPPORTING A LONGITUDINAL TEST TUBE, AND EQUIPMENT FOR DETERMINING THE MECHANICAL BENDING PROPERTIES OF SUCH A TEST TUBE

CROSS-REFERENCES TO RELATED APPLICATIONS

This application claims the benefit of the French patent application No. 1155389 filed on Jun. 20, 2011, the entire disclosures of which are incorporated herein by way of reference.

BACKGROUND OF THE INVENTION

The present invention relates to a device for the transverse retention of a longitudinal test specimen, notably having a stylized L-shaped or S-shaped cross section, and to an apparatus for the mechanical characterization of such a test specimen in bending.

The invention is particularly well suited, although not exclusively, to the three-point or four-point symmetric or asymmetric flexural characterization.

In the known way, three-point or four-point bending tests are used in order to study and characterize the resistance to loading of new materials (for example metallic materials, composite materials, etc.).

The principle behind these bending tests is to subject a test specimen made of a material that is to be tested, of given dimensions, to a deformation that is defined by a constant strain rate and to measure the force with which the said test specimen opposes this deformation. In this way it is possible to determine the mechanical behavior, the physical properties and the characteristics of the material of which the test specimen is made.

There are two families of bending test:
  simple bending tests (also known as three-point tests) which are defined by a single central pressure point at which the bending force is applied and two reaction points on which the respective ends of the test specimen rest; and
  four-point bending tests which are characterized by two central pressure points via which the bending force is applied and two reaction points supporting the ends of the test specimen.

Furthermore, the reaction points supporting the test specimen can be of two types, namely:
  either linear, in which case contact between the supports and the test specimen is tangential;
  or surface, in which case contact between the supports and the test specimen is defined by a contact face.

Whatever the type of contact, the main operating parameters for these test are the bending force applied to the test specimen and the distance separating the two opposite contact points of the reaction points supporting the test specimen.

Document FR2937731 already discloses an apparatus for the flexural characterization of a longitudinal test specimen having a lower face and an upper face that are substantially parallel. In particular, the apparatus comprises bearing means that have the ability to rotate about an axis with respect to a fixed support and attachment and adjustment means for adjusting the positioning of the test specimen relative to the bearing means. When the test specimen is deformed under the effect of the central force, the bearing means undergo a rotational movement about the axis of rotation so that the points of contact between the test specimen and the bearing means remain aligned with said axis of rotation.

However, the abovementioned apparatus proves to be ill suited to the flexural characterization of test specimens of a stylized S-shaped cross section defined by two lateral flanges joined together by an orthogonal web. This is because applying a bending force to such a test specimen retained by the bearing means of such an apparatus generally causes the web to tilt as a result of a moment generated by opposing forces applied to the lateral flanges.

It is an object of the present invention to overcome this disadvantage.

SUMMARY OF THE INVENTION

To this end, according to the invention, the device for the transverse retention of a longitudinal test specimen, comprising a web and at least one main flange connected to one end of said web, is notable in that it comprises:
  a body in which there is formed a housing which is shaped to house said test specimen transversally and which has a main bearing face against which one face of said web is intended to press; and
  mobile clamping means formed so as to press said web against said main bearing face.

Thus, by virtue of the invention, clamping a longitudinal portion of the web of such a test specimen in the housing which is configured using the clamping means makes it possible to prevent any tilting or movement of the web—and therefore of the test specimen—while a bending force is being applied thereto, making it possible for test specimens of stylized L-shaped or S-shaped (or even of stylized C-shaped or Z-shaped) cross sections to be retained by devices according to the invention and therefore makes three-point or four-point flexural characterization thereof a conceivable prospect.

In order further to improve the retention of a test specimen by the transverse retention device, said housing may comprise a first additional bearing face against which one face of said main flange is intended to press and said mobile clamping means for clamping said web may be formed so that they press said main flange against said first additional bearing face.

For preference, said mobile clamping means comprise:
  a moving part which has a contact face intended to press against another face of said web; and
  means for adjusting the intensity of the force applied to said web by said moving part.

In particular, said adjusting means may be in the form of at least one screw, passing through said body, which is able to press via one of its longitudinal ends against said moving part.

The transverse retention device may further comprise a removable cover able to close off said housing.

When said test specimen comprises an auxiliary flange, connected to said main flange by said web, said cover preferably comprises additional moving clamping means formed to apply a retention force to one face of said auxiliary flange.

Furthermore, in this case, said body may advantageously comprise a second additional bearing face against which said auxiliary flange is intended to be pressed by said additional clamping means.

In addition, said second additional bearing face may be mounted so that it can move, so as to be adjustable, for example in terms of height and inclination.

Advantageously, said main bearing face is covered, or formed, at least in part, with a material that has a low coefficient of friction, for example with polytetrafluoroethylene, allowing the test specimen to move longitudinally. In particular, when the test specimen, held in place by one or more devices according to the invention, is subjected to three- or four-point bending, the presence of a material with a low coefficient of friction ensures uniform distribution of the load applied to the test specimen, along the latter.

Moreover, the present invention also relates to an apparatus for the mechanical characterization in bending of a test specimen comprising a web and at least one main flange connected to the end of said web. According to the invention, said apparatus comprises at least two transverse retention devices as described hereinabove, which are able to retain the longitudinal ends of said test specimen.

Furthermore, said apparatus preferably comprises two supports which are connected to a fixed base and on which said transverse retention devices are respectively mounted with the ability to rotate.

In addition, said apparatus may comprise at least one additional transverse retention device positioned between the two end retention devices in the center thereof, and via which a bending force is applied to said test specimen.

BRIEF DESCRIPTION OF THE DRAWINGS

The attached figures will make it easy to understand how the invention may be embodied. In these figures, identical references denote elements that are similar.

DETAILED DESCRIPTION OF THE PREFERRED EMBODIMENTS

Figure 1:
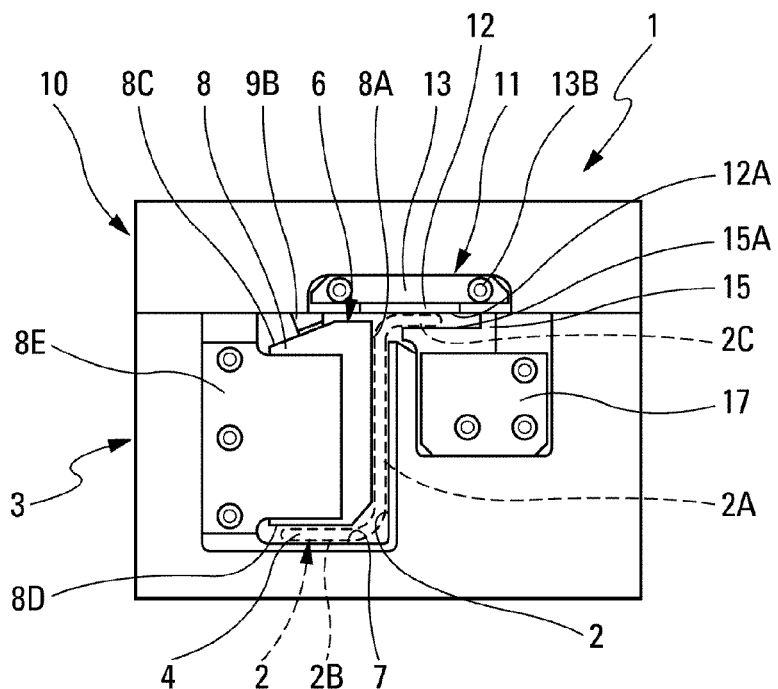
FIG. 1 is a schematic elevation of one exemplary embodiment of a device according to the present invention for the transverse retention of a longitudinal test specimen.
Figure 2:
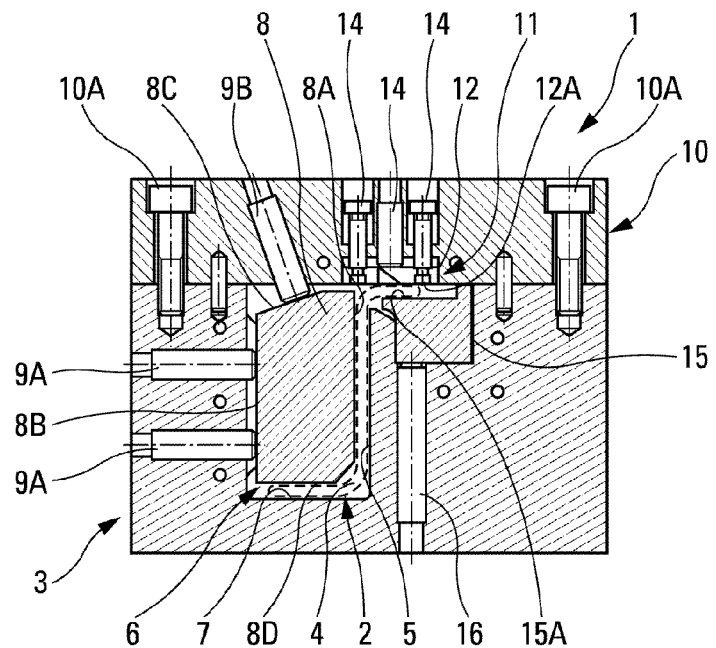
FIG. 2 is a schematic cross section of the transverse retention device of FIG. 1.

FIGS. 1 and 2 schematically depict one exemplary embodiment of a device 1 according to the invention for the transverse retention of a longitudinal test specimen 2 comprising a web 2A and two lateral flanges, a main flange 2B and an auxiliary flange 2C, connected to one another by said web 2A. The test specimen 2 therefore has a cross section in the shape of a stylized S.

According to the invention, the device 1 comprises:
  a body 3 in which there is formed a housing 4 which is shaped to house the test specimen 2 transversally and which has a main bearing face 5 against which one face of said web 2A is intended to press; and
  mobile clamping means 6 formed so as to press the web 2A against the main bearing face 5.

In addition, the housing 4 comprises a first additional bearing face 7 against which one face of the main flange 2B is intended to press.

The mobile clamping means 6 that clamp the web 2A are also formed so that they press the main flange 2B against the first additional bearing face 7. Of course, additional individual clamping means distinct from the clamping means 6 that clamp the web 2A are also conceivable, by way of alternative, for pressing the main flange 2B against the first additional bearing face 7.

In this example of the retention device 1 of the invention, the mobile clamping means 6 comprise:
  a flat moving part 8 which has a contact face 8A intended to press against another face of the web 2A. The moving part 8 is held in position by two lateral plates 8E, distributed one on either side of said part 8 and fixed removably to the body 3. The part 8 is therefore free between the two plates 8E; and
  means 9A and 9B for adjusting the intensity of the force applied to the web 2A by the moving part 8. The adjusting means are in the form of three screws, namely:
    two screws 9A, passing laterally through the body 3, emerging into the housing 4 to press against a face 8B of the part 8 which is opposite and parallel to the contact face 8A, making it possible to adjust the pressure applied by the part 8 to the web 2A; and
    a screw 9B presses against an inclined face 8C of the part 8, so as to adjust the pressure applied by the part 8 to the main flange 2B via its contact face. The screw 9B passes through a cover 10 detailed hereinafter.

As FIGS. 1 and 2 show, the device 1 further comprises the removable cover 10 able to close off the housing 4. Once the test specimen has been housed in the housing 4, the cover 10 is applied and attached to the body 3, for example using retaining screws 10A.

The cover 10 comprises additional mobile clamping means 11 formed to apply a retention force to one face of the auxiliary flange 2C facing it. These additional clamping means 11 comprise a flat moving part 12 having a contact face 12A intended to press against the auxiliary flange 2C. The moving part 12 is held in position by two lateral plates 13 distributed one on either side of the part 12 and fixed removably to the cover 10 by screws 13B.

Means 14, in the form of screws, allow the intensity of the pressure applied to the auxiliary flange 2C by the moving part 12 and the inclination of the face 12A to be adjusted so that with adjustment it can collaborate with the face of the auxiliary flange 2C opposite.

Moreover, the body 3 may comprise a second additional bearing face 15A against which the auxiliary flange 2C can be pressed using the additional clamping means 11.

The second additional bearing face 15A belongs to a flat moving part 15 mounted on the body 3 and held in position by removable plates 17. A screw 16 that passes transversally through the body 3 and presses against the part 15 allows the inclination of the face 15A to be modified to make it collaborate perfectly with the corresponding face opposite belonging to the auxiliary flange 2C.

It should be noted:
  that the faces 5, 7, 8A, 8D, 12A and 15A are advantageously made, at least superficially, of a material with a low coefficient of friction for example polytetrafluoroethylene; and
  that the clamping of the test specimen 2 by the moving parts 8, 12 and/or 15 is performed in such a way that the test specimen 2 can slip from the retention device 1 when a bending force is being applied to it.

Figure 3:
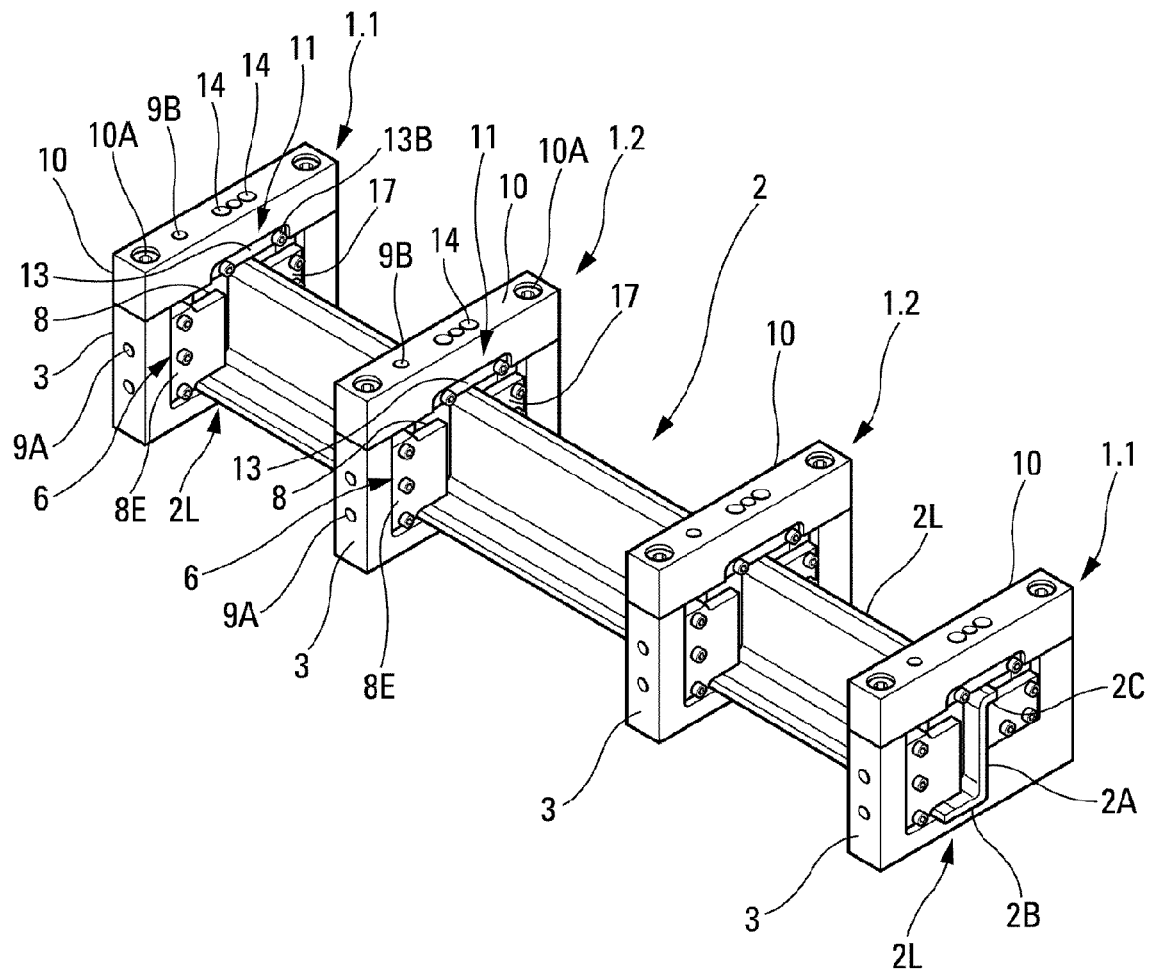
FIG. 3 is a schematic perspective depiction of a longitudinal test specimen that is to be tested and to which four retention devices according to that of FIG. 1 have been applied.

FIG. 3 is a perspective depiction of the longitudinal test specimen 2 that is to be tested, with four transverse retention devices 1.1 and 1.2 (identical to the transverse retention device 1 of FIG. 1) applied to it before they are mounted on an apparatus A for the flexural characterization detailed hereinafter. Of these transverse retention devices, two (hereinafter termed the end devices and referenced 1.1) are positioned at the respective longitudinal ends 2L of the test specimen 2, the other two (hereinafter referred to as the central devices and referenced 1.2) being distributed between the end devices 1.1, equidistant therefrom.

Arranging the retention devices 1.1 and 1.2 on the test specimen 2 in this way allows the specimen to undergo four-point bending testing. For a three-point bending test of the test specimen 2, just one central device 1.2 (rather than two) is needed, so that the number of transverse retention devices required is confined to three.

Figure 4:
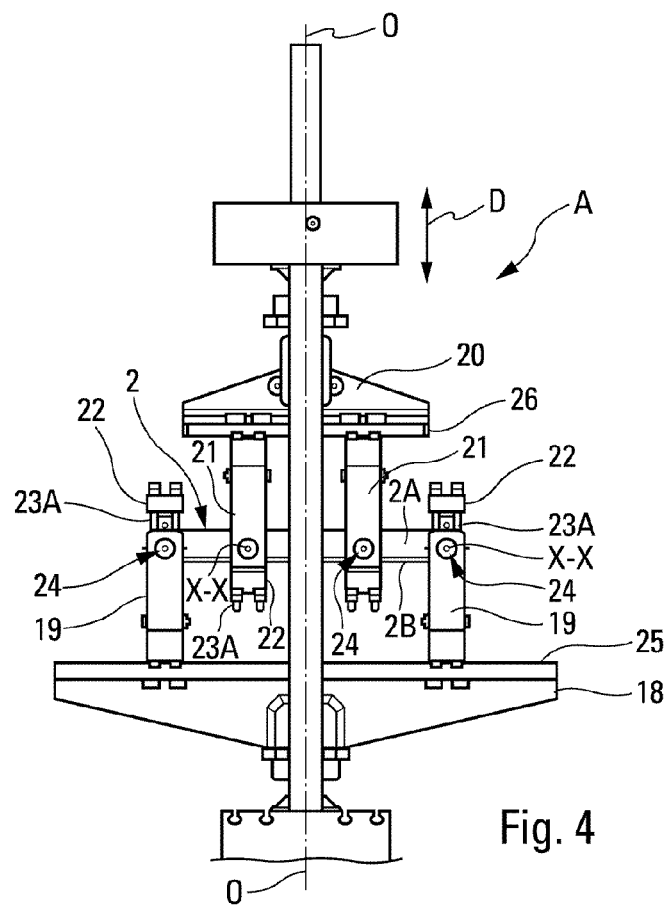
FIG. 4 is a schematic elevation of an example of an apparatus for the four-point flexural characterization of the test specimen of FIG. 3.

FIG. 4 illustrates an apparatus A for the four-point flexural characterization on which apparatus the transverse retention devices 1.1 and 1.2 of FIG. 3 have been mounted.

The apparatus A comprises a fixed base 18 to which two end supports 19 are attached to support the associated end retention devices 1.1 (which are used as reaction points). It also comprises a mobile auxiliary base 20 able to slide along a vertical axis O-O and to which two auxiliary supports 21 are attached to support the associated central retention devices 1.2.

Each transverse retention device, be it a central device 1.2 or an end device 1.1, is held fast, by clamping, to a fixture 22 (FIG. 5) mounted on a corresponding support 19, 21, which comprises:
- two transverse clamping plates 22A joined to one another at their lateral ends by threaded clamping rods 23A bearing clamping nuts, and
- two lateral clamping plates 22B orthogonal to the transverse plates and able to be pressed against the corresponding device 1.1, 1.2 by clamping means 23B.

Figure 5:
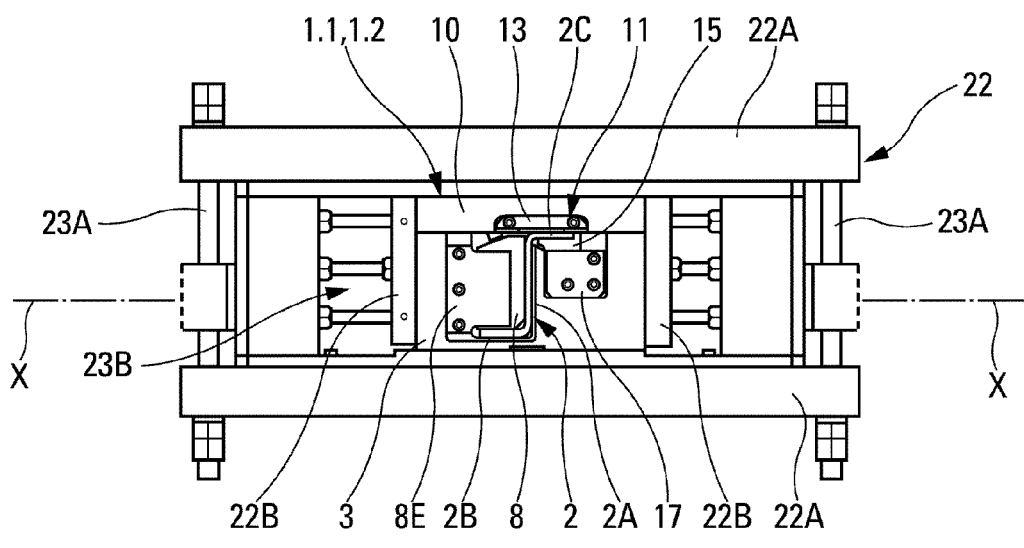
FIG. 5 is a schematic depiction of one example of a mobile fixture belonging to the apparatus of FIG. 4, to which a transverse retention device according to that of FIG. 1 is attached.

These plates 22A and 22B are intended to press against the lateral edges of the associated retention device 1.1, 1.2 as illustrated in FIG. 5.

Furthermore, each support 19, 21 comprises a bearing 23 of axis X-X about which the associated fixture 22 is mounted with the ability to rotate. Thus, during flexural characterization of a test specimen 2, the end retention devices 1.1 and central retention devices 1.2 can pivot about the axis of rotation X-X to follow the curvature of the test specimen 2 as a bending force is applied.

By virtue of the invention, during mechanical flexural characterization of the test specimen 2 using the apparatus A, the mobile base 20 slides along the axis O-O (this movement being symbolized by the arrow D in FIG. 4) so that a transverse force is applied to the test specimen 2 via the two central retention devices 1.2. Using the end transverse retention devices 1.1 and central transverse retention devices 1.2 according to the invention, the test specimen 2 cannot pivot when a bending force is applied.

It should be noted that the supports 19 and 21 may be mounted on respective slideways 25 and 26, so that the separation between the end devices 1.1 can be adjusted (by means of the slideway 25) and between the central devices 1.2 can be adjusted (by means of the slideway 26), for example to suit the length of the test specimen 2 to be tested.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A device for the transverse retention of a longitudinal test specimen, comprising a web and at least one main flange connected to one end of said web, comprising:
    a body in which there is formed a housing which is shaped to house said test specimen transversally and which has a main bearing face against which one face of said web is intended to press; and
    mobile clamping means formed so as to press said web against said main bearing face.

2. The device as claimed in claim 1, wherein:
    said housing comprises a first additional bearing face against which one face of said main flange is intended to press; and
    said mobile clamping means for clamping said web are configured and arranged so that they press said main flange against said first additional bearing face.

3. The device as claimed in claim 1, wherein said mobile clamping means comprise:
    a moving part which has a contact face intended to press against another face of said web; and
    means for adjusting the intensity of the force applied to said web by said moving part.

4. The device as claimed in claim 3, wherein said adjusting means are in the form of at least one screw, passing through said body, which screw presses via one of its longitudinal ends against said moving part.

5. The device as claimed in claim 1, further comprising a removable cover configured and arranged to close off said housing.

6. The device as claimed in claim 5, wherein said test specimen comprises an auxiliary flange, connected to said main flange by said web, and said cover comprises additional moving clamping means formed to apply a retention force to one face of said auxiliary flange.

7. The device as claimed in claim 6, wherein said body comprises a second additional bearing face against which said auxiliary flange is pressed by said additional clamping means.

8. The device as claimed in claim 7, wherein said second additional bearing face is mounted so that it can move.

9. The device as claimed in claim 1, wherein said main bearing face is covered, at least in part, with a material that has a low coefficient of friction.

10. The device as claimed in claim 9, wherein said low coefficient of friction material comprises of polytetrafluoroethylene.

11. An apparatus for the mechanical characterization in bending of a test specimen comprising a web and at least one main flange connected to the end of said web, comprising
    at least two transverse retention devices as specified in claim 1, which retain the longitudinal ends of said test specimen.

12. The apparatus as claimed in claim 11, further comprising two supports which are connected to a fixed base and on which said transverse retention devices are respectively rotatably mounted.

13. The apparatus as claimed in claim 11, further comprising at least one additional transverse retention device positioned between the two end retention devices in the center thereof, and via which a bending force is applied to said test specimen.

* * * * *